(12) United States Patent
Tateishi et al.

(10) Patent No.: US 7,988,991 B2
(45) Date of Patent: Aug. 2, 2011

(54) ADHESIVE PATCH

(75) Inventors: Tetsuro Tateishi, Tsukuba (JP); Takaaki Terahara, Tsukuba (JP); Naruhito Higo, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 457 days.

(21) Appl. No.: 10/469,612

(22) PCT Filed: Mar. 7, 2002

(86) PCT No.: PCT/JP02/02142
§ 371 (c)(1),
(2), (4) Date: Sep. 4, 2003

(87) PCT Pub. No.: WO02/069942
PCT Pub. Date: Sep. 12, 2002

(65) Prior Publication Data
US 2004/0096491 A1    May 20, 2004

(30) Foreign Application Priority Data
Mar. 7, 2001    (JP) .............................. P2001-063767

(51) Int. Cl.
*A61F 13/02* (2006.01)

(52) U.S. Cl. ......................... 424/448; 424/449; 424/484

(58) Field of Classification Search .................... None
See application file for complete search history.

(56) References Cited

U.S. PATENT DOCUMENTS

| 3,797,494 A | * | 3/1974 | Zaffaroni ...................... 424/434 |
| 4,814,168 A | | 3/1989 | Sablotsky et al. |
| 4,994,267 A | * | 2/1991 | Sablotsky ...................... 514/182 |
| 5,200,190 A | | 4/1993 | Azuma et al. |
| 5,474,783 A | | 12/1995 | Miranda et al. |
| 5,614,211 A | * | 3/1997 | Gale et al. ...................... 424/448 |
| 5,656,286 A | | 8/1997 | Miranda et al. |
| 5,820,878 A | * | 10/1998 | Hirano et al. .................. 424/449 |
| 5,866,157 A | * | 2/1999 | Higo et al. ..................... 424/448 |
| 6,024,976 A | | 2/2000 | Miranda et al. |
| 6,210,705 B1 | * | 4/2001 | Mantelle et al. ............... 424/448 |
| 6,231,885 B1 | | 5/2001 | Carrara |
| 6,461,636 B1 | * | 10/2002 | Arth et al. ...................... 424/449 |
| 2004/0028724 A1 | | 2/2004 | Terahara et al. |

FOREIGN PATENT DOCUMENTS

| EP | 0 364 211 A1 | 4/1990 |
| EP | 0 559 411 A1 | 9/1993 |
| EP | 0 913 158 A1 | 5/1999 |
| EP | 1 340 396 A1 | 9/2003 |
| JP | 6-9379 | 1/1994 |
| JP | 6-145052 A | 5/1994 |
| JP | 9-143066 A | 6/1997 |
| JP | 09-301854 A | 11/1997 |
| JP | 9-301854 A | 11/1997 |
| JP | 10-179711 A | 7/1998 |
| JP | 11-152224 | 6/1999 |
| JP | 2001-048783 | 2/2001 |
| JP | P2001-48783 A | 2/2001 |
| WO | WO 90/07940 A | 7/1990 |
| WO | WO 95/18603 | 7/1995 |

OTHER PUBLICATIONS

Email from Susan Lydzinski, Technical Marketing Specialist, National Adhesives, dated Oct. 17, 2007.*

Journal of New Remedies & Clinics, vol. 48, No. 8, pp. 1015-1024 (1999).

* cited by examiner

*Primary Examiner* — Robert A Wax
*Assistant Examiner* — Hasan S Ahmed
(74) *Attorney, Agent, or Firm* — The Nath Law Group; Susanne M. Hopkins; Ari G. Zytcer

(57) ABSTRACT

A patch agent of the present invention comprises a support, and an adhesive layer laid on the support and containing an adhesive base and a drug, wherein the adhesive base contains an acrylic polymer substantially having no carboxyl and no hydroxyl in molecules thereof, and a rubber-based polymer, so as to achieve sufficiently high skin permeability of the drug and preparation properties. Accordingly, the present invention enables administration of the drug through skin to be implemented with drug administration effect at a sufficiently high level and on a stable basis.

5 Claims, No Drawings

ADHESIVE PATCH

CROSS-REFERENCED APPLICATIONS

This application is a National phase of International Application PCT/JP02/02142, filed Mar. 7, 2002, which designated the U.S. and that International Application was not published under PCT Article 21(2) in English.

TECHNICAL FIELD

The present invention relates to a patch agent and, more particularly, to a patch agent using an acrylic polymer and a rubber-based polymer as an adhesive base.

BACKGROUND ART

The conventionally known drug administration methods include oral administration methods using tablets, capsules, syrup, etc., and attempts have been made in recent years to administrate the drugs through skin by use of patch agents. Since the administration method using the patch agents has the advantages of decrease in the number of administration times, improvement in compliance, easiness of administration and discontinuation thereof, etc., in addition to solving problems in the oral administration methods, it is thus expected to be a drug administration method useful, particularly, in treatments of elderly and child patients.

Incidentally, the corneum of normal skin has a barrier function of preventing foreign matter from getting into the body, and it is thus often the case that the base used in the ordinary patch agents fails to achieve satisfactory transdermal absorption of a medicinal component blended therein. In addition, the corneum is highly fat-soluble, and thus the drugs demonstrate extremely low permeability in general. For this reason, it becomes necessary to enhance the transdermal absorbability of the drug through the corneum of skin, for administering the drug through skin by use of the patch agent.

Research thus has been conducted heretofore to implement optimization of the composition of an absorption promoter including various transdermal absorption promoting agents, and an adhesive component. Particularly, concerning the adhesive base of the patch agent, it is important to design the adhesive base so as to blend various (adhesive) polymers and provide it with satisfactory preparation properties and optimal drug solubility, and from this point of view, polymer materials such as acrylic polymers, rubber-based polymers, silicone-based polymers, or the like are generally used as pressure-sensitive adhesive bases.

These polymer materials demonstrate different features as to the transdermal absorbability of the drug. For example, the rubber-based polymers with relatively low solubility of the drug have high transdermal absorbability of the drug but have a limitation to amounts of the drug that can be included; therefore, drug absorption rates are likely to drop during application of the patch agent, so that the level of the drug in the blood decreases, so as to fail to achieve continuous effect (Journal of New Remedies & Clinics, 48, 1015-1-24, 1999). The rubber-based polymers have low solubility of the drug and readily cause crystallization of the drug in the preparation with a lapse of time, so as to fail to achieve satisfactory stability in certain cases.

The acrylic polymers demonstrate higher solubility of the drug but lower absorption of the drug than the rubber-based polymers. For this reason, the concentration of the drug needs to be increased in order to achieve necessary absorption of the drug in the patch agents using the acrylic polymers, and this can cause failure in achieving satisfactory preparation properties in formulation, or increase the cost.

In order to avoid the phenomena occurring in the cases using the above polymers, proposals were thus made on methods using the adhesive base containing a blend of polymers.

For example, National Publication of Translated Version of PCT Application, Publication No. H04-502719 discloses pressure-sensitive adhesive dermal compositions containing a blend of a polymer mixture of a vinyl acetate/ethylene copolymer and an acrylic polymer, a natural or synthetic rubber, and a tackifier. In addition, National Publication of Translated Version of PCT Application, Publication No. H09-511987 discloses pressure-sensitive adhesive compositions containing a polyacrylate, a rubber, a drug, and a soluble polyvinylpyrrolidone.

DISCLOSURE OF THE INVENTION

Even in the case where the above conventional pressure-sensitive adhesive compositions were applied to the adhesive base of the patch agent, the skin permeability of the drug was not always satisfactory, and it was very difficult to achieve sufficient treatment effect by the drug. In the case using the soluble polyvinylpyrrolidone, a satisfactory adhesive property became unlikely to yield and the preparation properties were insufficient, including complexity of the production process thereof.

The present invention has been accomplished in view of the problems in the prior art as discussed above, and an object of the invention is to provide a patch agent capable of achieving sufficiently high skin permeability of the drug and preparation properties and presenting the drug administration effect at a sufficiently high level and on a stable basis in administration of the drug through skin.

The Inventors have conducted elaborate research in order to achieve the above object and found that most of the acrylic polymers included in the above conventional pressure-sensitive adhesive compositions had carboxyls (—COOH) and hydroxyls (—OH) in molecules thereof as reactive sites for crosslinking, it was very difficult to achieve both satisfactory skin permeability of the drug and satisfactory preparation properties in the patch agent using such acrylic polymers, and the above problems were solved by using the adhesive base containing an acrylic polymer substantially having no carboxyl and no hydroxyl in molecules, and a rubber-based polymer, thus completing the present invention.

Namely, a patch agent of the present invention comprises a support, and an adhesive layer laid on the support and containing an adhesive base and a drug, wherein the adhesive base contains an acrylic polymer substantially having no carboxyl and no hydroxyl in molecules thereof, and a rubber-based polymer.

In the patch agent of the present invention, the skin permeability of the drug and the preparation properties both can be sufficiently enhanced by using the adhesive base containing the acrylic polymer substantially having no carboxyl (—COOH) and no hydroxyl (—OH) in molecules thereof, and the rubber-based polymer, whereby it becomes feasible to present the drug administration effect at a sufficiently high level and on a stable basis in administration of the drug through skin.

In the present invention, the acrylic polymer is preferably at least one selected from the group consisting of: a block copolymer of a polymethyl methacrylate and a polyacrylate containing at least one selected from the group consisting of 2-ethylhexyl acrylate, butyl acrylate, diacetone acrylamide, or tetraethylene glycol dimethacrylate; a 2-ethylhexyl acrylate.N-vinyl-2-pyrrolidone.1,6-hexane glycol dimethacrylate copolymer; an aminoalkylmethacrylate copolymer E; and a 2-ethylhexyl acrylate.vinyl acetate copolymer; and more preferably at least one selected from the group consisting of a 2-ethylhexyl acrylate.N-vinyl-2-pyrrolidone.1,6-hexane glycol dimethacrylate copolymer and a 2-ethylhexyl acrylate.vinyl acetate copolymer.

In the present invention, the rubber-based polymer is preferably at least one selected from the group consisting of a styrene-isoprene-styrene block copolymer, a polyisobutylene, an isoprene rubber, a styrene-butadiene-styrene block copolymer, a styrene-butadiene rubber, and a silicone rubber; and more preferably at least one selected from the group consisting of a styrene-isoprene-styrene block copolymer and a polyisobutylene.

In the present invention, particularly preferably, the acrylic polymer is at least one selected from the group consisting of a 2-ethylhexyl acrylate.N-vinyl-2-pyrrolidone.1,6-hexane glycol dimethacrylate copolymer and a 2-ethylhexyl acrylate.vinyl acetate copolymer, and the rubber-based polymer is a styrene-isoprene-styrene block copolymer.

Furthermore, in the present invention, the drug is preferably at least one selected from the group consisting of basic drugs and pharmacologically acceptable salts thereof; and more preferably at least one selected from the group consisting of pergolide, pharmacologically acceptable salts of pergolide, oxybutynin, and pharmacologically acceptable salts of oxybutynin.

BEST MODE FOR CARRYING OUT THE INVENTION

Preferred embodiments of the present invention will be described below in detail.

The patch agent of the present invention is a patch agent comprising a support; and an adhesive layer laid on the support and containing an adhesive base and a drug, wherein the adhesive base contains an acrylic polymer substantially having no carboxyl and no hydroxyl in molecules thereof, and a rubber-based polymer.

There are no specific restrictions on the support used in the patch agent of the present invention as long as it can support the adhesive layer; it can be any of stretchable or unstretchable supports. The support is, specifically, fabric, nonwoven fabric, polyurethane, polyester, polyvinyl acetate, polyvinylidene chloride, polyethylene, polyethylene terephthalate, an aluminum sheet, or a composite material of two or more selected from these, or the like.

There are no specific restrictions on the thickness of the support according to the present invention, but the thickness is determined preferably in the range of 5 to 1000 μm. If the thickness of the support is less than the lower limit easiness will tend to degrade in a work of applying the patch agent; if the thickness of the support exceeds the upper limit on the other hand productivity will tend to degrade in a work of cutting the support or the patch agent in the production process of the patch agent.

In the patch agent of the present invention, the adhesive layer containing the adhesive base and the drug is laid on the foregoing support. Here the adhesive base according to the present invention is one containing the acrylic polymer substantially having no carboxyl and no hydroxyl in molecules thereof, and the rubber-based polymer.

The acrylic polymer substantially containing no carboxyl (carboxyl group, —COOH) and no hydroxyl (—OH) in its molecules according to the present invention refers to an acrylic polymer excluding carboxyls and hydroxyls that can act as reactive sites in crosslinking in the molecules thereof. Favorable examples of the acrylic polymer include a block copolymer of a polymethyl methacrylate and a polyacrylate containing at least one selected from the group consisting of 2-ethylhexyl acrylate, butyl acrylate, diacetone acrylamide, or tetraethylene glycol dimethacrylate; a 2-ethylhexyl acrylate.N-vinyl-2-pyrrolidone.1,6-hexane glycol dimethacrylate copolymer; an aminoalkylmethacrylate copolymer E; and a 2-ethylhexyl acrylate.vinyl acetate copolymer. Commercial product examples of the acrylic polymer substantially containing no carboxyl and no hydroxyl in molecules thereof include DURO-TAK87-2097, DURO-TAK87-4098, etc. available from National Starch & Chemical Co. Among these, the acrylic polymer is more preferably the 2-ethylhexyl acrylate.N-vinyl-2-pyrrolidone.1,6-hexane glycol dimethacrylate copolymer and/or the 2-ethylhexyl acrylate.vinyl acetate copolymer, because the use thereof tends to enhance both the skin permeability of the drug and the preparation properties more. One of these acrylic polymers may be used alone, or two or more thereof may be used in combination.

In the production process of the above acrylic polymer, if source monomers contain a small amount of monomers having carboxyls and/or hydroxyls as impurities, or if side reaction such as heat deterioration takes place during polymerization, carboxyls and/or hydroxyls originating in the impurities can be introduced into the resultant acrylic polymer; it is contemplated that such acrylic polymers are encompassed within the acrylic polymer substantially having no carboxyl and no hydroxyl in molecules thereof, as long as they do not degrade the sufficiently high skin permeability of the drug and sufficiently high preparation properties that the patch agent of the present invention has.

However, the carboxyls and hydroxyls in the acrylic polymer according to the present invention are preferably as few as possible, even if they are derived from the mixing of impurities and the side reaction such as heat deterioration in the production process thereof.

There are no specific restrictions on the content of the acrylic polymer according to the present invention, but the content is determined preferably in the range of 0.2 to 60% by weight, more preferably in the range of 0.5 to 50% by weight, and still more preferably in the range of 1 to 40% by weight on the basis of the total weight of the adhesive base. If the content of the acrylic polymer according to the present invention is less than the lower limit the skin permeability of the drug will tend to be insufficient; if the content exceeds the upper limit on the other hand the patch agent will tend to have insufficient cohesion.

The rubber-based polymer according to the present invention is a natural or synthetic, elastomeric polymer. Favorable examples of the rubber-based polymer include a styrene-isoprene-styrene block copolymer, a polyisobutylene, an isoprene rubber, a styrene-butadiene-styrene block copolymer, a styrene-butadiene rubber, a silicone rubber, and so on. Among these, the styrene-isoprene-styrene block copolymer or polyisobutylene is more preferably used, because the skin permeability of the drug and the preparation properties both tend to be higher therewith. One of these rubber-based polymers may be used alone, or two or more thereof may be used in combination.

There are no specific restrictions on the content of the rubber-based polymer according to the present invention, but the content is determined preferably in the range of 0.2 to 60% by weight, more preferably in the range of 0.5 to 50% by weight, and still more preferably in the range of 1 to 40% by weight on the basis of the total weight of the adhesive base. If the content of the rubber-based polymer is less than the lower limit the skin permeability of the drug will tend to become insufficient; if the content exceeds the upper limit on the other hand the adhesion of the patch agent will tend to become insufficient.

Favorable combinations of the acrylic polymer and the rubber-based polymer according to the present invention include the following combinations (1) to (4):

(1) a combination of the block copolymer of the polymethyl methacrylate and the polyacrylate containing at least one selected from the group consisting of 2-ethylhexyl acrylate, butyl acrylate, diacetone acrylamide, or tetraethylene glycol dimethacrylate, with the styrene-isoprene-styrene block copolymer;

(2) a combination of the 2-ethylhexyl acrylate.N-vinyl-2-pyrrolidone.1,6-hexane glycol dimethacrylate copolymer with the styrene-isoprene-styrene block copolymer;

(3) a combination of the 2-ethylhexyl acrylate.vinyl acetate copolymer with the styrene-isoprene-styrene block copolymer;

(4) a combination of the aminoalkylmethacrylate copolymer E, the styrene-isoprene-styrene block copolymer, and the polyisobutylene. Among these, (1) the combination of the 2-ethylhexyl acrylate.vinyl acetate copolymer with the styrene-isoprene-styrene block copolymer, and (2) the combination of the 2-ethylhexyl acrylate.N-vinyl-2-pyrrolidone.1,6-hexane glycol dimethacrylate copolymer with the styrene-isoprene-styrene block copolymer are particularly preferred, because they can achieve both the skin permeability of the drug and the preparation properties at a higher level.

In the adhesive layer according to the present invention, the drug is blended in the foregoing adhesive base. There are no specific restrictions on the drug used in the present invention, and specific examples of the drug include hypnotic-sedatives (flurazepam hydrochloride, rilmazafone hydrochloride, phenobarbital, amobarbital, etc.), antipyretic antiphlogistic analgesics (butorphanol tartrate, perisoxal citrate, acetoaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, etc.), steroid antiphlogistics (hydrocortisone, prednisolone, dexamethasone, betamethasone, etc.), stimulant-antihypnotics (methamphetamine hydrochloride, methylphenidate hydrochloride, etc.), drugs for psychoneurotic disorders (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazadone, lofepramine, milnacipran, duloxetine, venlafaxine, chlorpromazine hydrochloride, thioridazine, diazepam, meprobamate, etizolam, etc.), hormones (estradiol, estriol, progesterone, norethisterone acetate, metenolon acetate, testosterone, etc.), local anesthetics (lidocaine hydrochloride, procaine hydrochloride, tetracaine hydrochloride, dibucaine hydrochloride, propitocaine hydrochloride, etc.), drugs for urinary organs (oxybutynin hydrochloride, tamsulosin hydrochloride, propiverine hydrochloride, etc.), skeletal muscle relaxants (tizanidine hydrochloride, eperisone hydrochloride, pridinol mesylate, suxamethonium chloride, etc.), drugs for genital organs (ritodrine hydrochloride and meladrine tartrate), antiepileptics (sodium valproate, clonazepam, carbamazepine, etc.), drugs for autonomic nerve (carpronium chloride, neostigmine bromide, bethanechol chloride, etc.), antiparkinson drugs (pergolide mesylate, bromocriptine mesylate, trihexyphenidyl hydrochloride, amantadine hydrochloride, ropinirole hydrochloride, talipexole hydrochloride, cabergoline, droxidopa, biperiden, selegiline hydrochloride, etc.), diuretics (hydroflumethiazide, furosemide, etc.), respiratory stimulants (lobeline hydrochloride, dimorpholamine, naloxone hydrochloride, etc.), antimigraine drugs (dihydroergotamine mesylate, sumatriptan, ergotamine tartrate, flunarizine hydrochloride, cyproheptadine hydrochloride, etc.), antihistamines (clemastine fumarate, diphenhydramine tannate, chlorpheniramine maleate, diphenylpyraline hydrochloride, promethazine, etc.), bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, etc.), cardiacs (isoprenaline hydrochloride, dopamine hydrochloride, etc.), coronary vasodilators (diltiazem hydrochloride, verapamil hydrochloride, isosorbide nitrate, nitroglycerin, nicorandil, etc.), peripheral vasodilators (nicametate citrate, tolazoline hydrochloride, etc.), antismoking agents (nicotine and others), cardiovascular drugs (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride, etc.), antiarrhythmics (propranolol hydrochloride, alprenolol hydrochloride, procainamide hydrochloride, mexiletine hydrochloride, nadolol, disopyramide, etc.), drugs for malignant ulcers (cyclophosphamide, fluorouracil, degafur, procarbazine hydrochloride, ranimustine, irinotecan hydrochloride, fluridine, etc.), antilipemic agents (pravastatine, simvastatin, bezafibrate, probucol, etc.), drugs for lowering the level of blood sugar (gliben clamid, chlorpropamide, tolbutamide, glymidine sodium, glybuzole, buformin hydrochloride), drugs for peptic ulcers (proglumide, cetraxate hydrochloride, spizofurone, cimetidine, glycopyrronium bromide), cholagogues (ursodesoxycholic acid, osalmid, etc.), gastrointestinal agents (domperidone, cisapride, etc.), drugs for liver disorders (tiopronin and others), antiallergic agents (ketotifen fumarate, azelastin hydrochloride, etc.), antiviral agents (aciclovir and others), antidinics (betahistine mesylate, diphenidol hydrochloride, etc.), antibiotics (cefaloridine, cefdinir, cefpodoxime proxetil, cefaclor, clarithromycin, erythromycin, methyl erythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, etc.), drugs for habitual addiction (cyanamide and others), anorectics (mazindol and others), chemotherapeutics (isoniazid, ethionamide, pyrazinamide, etc.), blood coagulation accelerants (ticlopidine hydrochloride and warfarin potassium), drugs for Alzheimer's disease (physostigmine, donepezil hydrochloride, tacrine, arecoline, xanomeline, etc.), serotonin-receptor antagonist antiemetics (ondansetron hydrochloride, granisetron hydrochloride, ramosetron hydrochloride, azasetron hydrochloride, etc.), antipodagrics (colchicine, probenecid, sulfinpyrazone, etc.), narcotic analgesics (fentanyl citrate, morphine sulfate, morphine hydrochloride, codeine phosphate, cocaine hydrochloride, pethidine hydrochloride, etc.), and other drugs, or pharmacologically acceptable inorganic or organic salts thereof. Among these drugs, the drug used is selected preferably from the basic drugs or pharmacologically acceptable salts thereof and more preferably from pergolide, pharmacologically acceptable salts of pergolide, oxybutynin, and pharmacologically acceptable salts of oxybutynin. One of these drugs may be used alone, or two or more thereof may be used in combination.

The content of the drug according to the present invention is properly selected depending upon a type of the drug and other factors, but it is preferably 0.1-50% by weight on the basis of the total weight of the compounds included in the adhesive layer. If the content of the drug is less than the lower limit the skin permeability of the drug will tend to become insufficient; if it exceeds the upper limit on the other hand skin irritation will tend to increase.

The adhesive layer according to the present invention preferably further contains an organic acid, in addition to the above-stated adhesive base and drug. Examples of the organic acid include aliphatic (mono, di, or tri) carboxylic acids (acetic acid, propionic acid, citric acid, isobutyric acid, caproic acid, caprylic acid, lactic acid, maleic acid, pyruvic acid, oxalic acid, succinic acid, tartaric acid, etc.), aromatic carboxylic acids (phthalic acid, salicylic acid, benzoic acid, acetylsalicylic acid, etc.), alkylsulfonic acids (methane sulfonic acid, ethane sulfonic acid, propylsulfonic acid, butane sulfonic acid, polyoxyethylene alkyl ether sulfonic acid, etc.), alkylsulfonic acid derivatives (N-2-hydroxyethylpiperidine-N'-2-ethanesulfonic acid, cholic acid derivatives (dehydrochlolic acid and others), or salts thereof, and so on. Among these organic acids, the organic acid is selected preferably from monocarboxylic acids or alkylsulfonic acids, and is, particularly preferably, acetic acid. One of these organic acids may be used alone, or two or more thereof may be used in combination.

There are no specific restrictions on the content of the organic acid according to the present invention, but the content is determined preferably in the range of 0.01 to 20% by weight, more preferably in the range of 0.1 to 15% by weight, and still more preferably in the range of 0.1 to 10% by weight on the basis of the total weight of the compounds included in the adhesive layer. If the content of the organic acid is less than the lower limit the effect will be insufficient in improving the skin permeability of the drug by the blending of the organic acid; if the content exceeds the upper limit on the other hand skin irritation will tend to increase.

The adhesive layer of the patch agent of the present invention may also contain an absorption promoter, in addition to the above-stated adhesive base and drug and the organic acid blended according to need. The absorption promoter according to the present invention can be any well-known compound whose absorption promoting action in skin is acknowledged, and specific examples of such compounds include C6-C20 fatty acids, fatty alcohols, fatty acid esters, amides, or ethers; aromatic organic acids, aromatic alcohols, aromatic organic acid esters, or ethers, and so on. These compounds may be saturated or unsaturated compounds and may be straight, branched, or cyclic compounds. Furthermore, the absorption promoter according to the present invention may be selected from lactates, acetates, monoterpene base compounds, sesquiterpene base compounds, Azone, Azone derivatives, glycerin fatty acid esters, propylene glycol fatty acid esters, sorbitan fatty acid esters (Span family), polysorbate base compounds (Tween family), polyethyleneglycol fatty acid esters, polyoxyethylene hardened castor oil compounds (HCO family), polyoxyethylene alkylethers, sucrose fatty acid esters, vegetable oils, and so on. Among these absorption promoters, the absorption promoter according to the present invention is selected preferably from caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerol monocaprylate, glycerol monocaprate, glycerol monolaurate, glycerol monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane, and olive oil and more preferably from lauryl alcohol, myristyl alcohol, isostearyl alcohol, lauric acid diethanolamide, glycerol monocaprylate, glycerol monocaprate, glycerol monooleate, sorbitan monolaurate, propylene glycol monolaurate, polyoxyethylene lauryl ether, and pirotiodecane. One of these absorption promoters may be used alone, or two or more thereof may be used in combination.

There are no specific restrictions on the content of the absorption promoter according to the present invention, but the content is determined preferably in the range of 0.01 to 20% by weight, more preferably in the range of 0.05 to 10% by weight, and still more preferably in the range of 0.1 to 5% by weight on the basis of the total weight of the compounds included in the adhesive layer. If the content of the absorption promoter is less than the lower limit the effect will tend to become insufficient in improving the skin permeability of the drug by the blending of the absorption promoter; if the content exceeds the upper limit on the other hand irritation to skin such as edema or the like will tend to increase.

The adhesive layer according to the present invention may further contain a plasticizer. The plasticizer used in the present invention is selected, specifically, from petroleum oils (paraffinic process oils, naphthenic process oils, aromatic process oils, etc.), squarane, squalene, plant oils (olive oil, camelia oil, castor oil, tall oil, peanut oil), silicone oil, dibasic acid esters (dibutyl phathalate, dioctyl phthalate, etc.), liquid rubbers (polybutene and liquid isoprene rubber), liquid fatty acid esters (isopropyl myristate, hexyl laurate, diethyl sebacate, diisopropyl sebacate, etc.), diethylene glycol, polyethylene glycol, glycol salicylate, propylene glycol, dipropylene glycol, triacetine, triethyl citrate, crotamiton, and so on. Among these plasticizers, the plasticizer according to the present invention is selected particularly preferably from liquid paraffin, liquid polybutene, crotamiton, diethyl sebacate, and hexyl laurate. One of these plasticizers may be used alone, or two or more thereof may be used in combination.

There are no specific restrictions on the content of the plasticizer according to the present invention, but the content is determined preferably in the range of 5 to 70% by weight, more preferably in the range of 10 to 60% by weight, and still more preferably in the range of 10 to 50% by weight on the basis of the total weight of the compounds included in the adhesive layer. If the content of the plasticizer is less than the lower limit the effect will tend to be insufficient in improving the cohesion of the patch agent by the blending of the plasticizer; if the content exceeds the upper limit on the other hand the skin permeability of the drug will tend to be insufficient.

The adhesive layer according to the present invention may contain a tackifier resin. Specific examples of the tackifier resin used in the present invention include rosin derivatives (rosin, glycerin ester of rosin, hydrogenated rosin, glycerin ester of hydrogenated rosin, pentaerythritol ester of rosin, etc.), alicyclic saturated hydrocarbon resins (ARKON P100 (available from ARAKAWA CHEMICAL INDUSTRIES, LTD.) and others), aliphatic hydrocarbon resins (Quintone B-170 (available from ZEON CORPORATION) and others), terpene resins (CLEARON P-125 (available from YASUHARA CHEMICAL CO., LTD.) and others), maleic acid resins, and so on; among these, the tackifier resin is selected preferably from glycerin ester of hydrogenated rosin, the alicyclic saturated hydrocarbon resins, the aliphatic hydrocarbon resins, and the terpene resins.

There are no specific restrictions on the content of the tackifier resin according to the present invention, but the content is determined preferably in the range of 5 to 70% by weight, more preferably in the range of 5 to 60% by weight, and still more preferably in the range of 10 to 50% by weight on the basis of the total weight of the compounds included in the adhesive layer. If the content of the tackifier resin is less than the lower limit the effect will tend to be insufficient in improving the adhesion of the patch agent by the blending of the tackifier resin; if the content exceeds the upper limit on the other hand irritation to skin will tend to increase upon release of the patch agent.

Furthermore, the present invention permits an antioxidant, a filler, a crosslinking agent, an antiseptic, an ultraviolet absorber, and/or the other additive to be blended in the adhesive layer as occasion demands. The antioxidant according to the present invention is selected preferably from tocopherol and ester derivatives thereof, ascorbic acid, ascorbic acid stearic acid esters, nordihydroguaiaretic acid, dibutyl hydroxytoluene (BHT), and butyl hydroxyanisole;

the filler is selected preferably from calcium carbonate, magnesium carbonate, silicates (e.g., aluminum silicate, magnesium silicate, etc.), silic acid, barium sulfate, calcium sulfate, calcium zincate, zinc oxide, and titanium oxide;

the crosslinking agent is selected desirably from thermosetting resins such as amino resins, phenol resins, epoxy resins, alkyd resins, unsaturated polyesters, and the like, isocyanate compounds, block isocyanate compounds, organic crosslinking agents, and inorganic crosslinking agents such as metals, metal compounds, or the like. The antiseptic is selected preferably from ethyl parahydroxybenzoate, propyl parahydroxybenzoate, and butyl parahydroxybenzoate;

the ultraviolet absorber is selected preferably from p-aminobenzoic acid derivatives, anthranilic acid derivatives, salicylic acid derivatives, coumarin derivatives, amino acid base compounds, imidazoline derivatives, pyrimidine derivatives, and dioxane derivatives.

There are no specific restrictions on the content of each of the above antioxidant, filler, crosslinking agent, antiseptic, and ultraviolet absorber, but the total amount of the antioxidant, filler, crosslinking agent, antiseptic, and ultraviolet absorber is determined preferably in the range of 0 to 10% by weight, more preferably in the range of 0 to 5% by weight, and still more preferably in the range of 0 to 2% by weight on the basis of the total weight of the compounds included in the adhesive layer.

There are no specific restrictions on how to place the adhesive layer of the above composition on the support, but the patch agent of the present invention can be made, for example, by thermally melting the adhesive base and the drug, and a mixture of the above other components added according to need and applying the molten mixture onto the support. In the case where the patch agent of the present invention further comprises release paper on the adhesive layer, the patch agent of the present invention can be made by first applying the above molten mixture onto the release paper and thereafter adhering the support onto the coating surface, or by applying the above molten mixture onto the support and then adhering the release paper onto the coating surface.

Furthermore, the patch agent of the present invention can also be obtained by using a coating solution in which the above mixture is melted in a solvent such as toluene, hexane, ethyl acetate, or the like, instead of the thermal melting of the above mixture.

Here the patch agent of the present invention may be one including one adhesive layer, or may be one including two or more adhesive layers unless the skin permeability of the drug is degraded thereby.

There are no specific restrictions on the thickness of the adhesive layer according to the present invention, but the thickness is preferably in the range of 20 to 200 µm. If the thickness of the adhesive layer is less than the lower limit the skin permeability of the drug will tend to be insufficient; if the thickness exceeds the upper limit on the other hand there will tend to occur a phenomenon in which the adhesive remains on the skin after applied (adhesive remainder).

Furthermore, in the case where the patch agent of the present invention comprises the release paper, the release paper is selected, specifically, from films of polyesters such as polyethylene terephthalate or the like, polyvinyl chloride, and polyvinylidene chloride, laminate films of quality paper and polyolefins, and so on. In these release papers, the surface in contact with the adhesive layer is preferably siliconized to enhance easiness in the work of releasing the release paper from the patch agent.

EXAMPLES

The present invention will be described below in further detail on the basis of Examples and Comparative Examples, but it is noted that the present invention is by no means intended to be limited to the Examples below. In the Examples below, "%" means "% by weight" unless otherwise stated.

Example 1

Fabrication of Patch Agent

Sertraline, pirotiodecane, and liquid paraffin were put into a mortar and mixed well. This mixture was added into a mixed solution consisting of a styrene-isoprene-styrene block copolymer, an acrylic polymer substantially having no carboxyl and no hydroxyl (a 2-ethylhexyl acrylate.vinyl acetate copolymer), an alicyclic saturated hydrocarbon resin (ARKON P-100 available from ARAKAWA CHEMICAL INDUSTRIES, LTD.), ethyl acetate, and toluene to prepare a coating solution having the following composition:

styrene-isoprene-styrene block copolymer 20.0%
acrylic polymer 10.0%
alicyclic saturated hydrocarbon resin 32.0%
liquid paraffin 30.0%
pirotiodecane 3.0%
sertraline 5.0%.

Then the resultant coating solution was applied onto polyethylene terephthalate release paper, and dried to remove the solvent to form the adhesive layer, and a polyethylene terephthalate support was attached to the adhesive layer to obtain the objective patch agent.

(Skin Permeability Test)

Using the patch agent obtained, the skin permeability test was conducted according to the following procedure.

First, skin was peeled off from the back of a hairless mouse, and was mounted with the corium side as a receptor-side layer in a flow through cell with warm water of 37° C. circulating in the periphery. Then the patch agent of Example 1 or Comparative Example 1 (both having the preparation application area of 5 cm$^2$) was applied onto the corneum side of the skin, physiological saline was used as a receptor layer, the receptor solution was sampled at 5 ml/hr at intervals of two hours over twenty four hours, the flow rate thereof was measured, and the concentration of the drug was measured by high performance liquid chromatography. The permeation rate of the drug per hour was calculated from the measured values obtained, and the permeation rate of the drug was determined per unit area of the skin in a steady state. The result obtained is presented in Table 1.

(Test of Preparation Properties)

The patch agent obtained was subjected to measurement of adhesion with a probe tack tester and a peel tester and measurement of cohesion with a creep meter, and the preparation properties thereof were evaluated on the basis of the following criteria:

A: sufficient in both adhesion and cohesion;
B: insufficient in at least one of adhesion and cohesion.

The result obtained is presented in Table 1.

Comparative Example 1

A patch agent was prepared in the same manner as in Example 1 except that an acrylic polymer having carboxyls (2-ethylhexyl acrylate.vinyl acetate-methacrylate copolymer) was used instead of the acrylic polymer used in Example 1, and the patch agent was subjected to the skin permeability test and the preparation property test. The results obtained are presented in Table 1.

TABLE 1

| | Permeation rate [µg · h$^{-1}$ · m$^{-2}$] | Preparation properties |
|---|---|---|
| Example 1 | 20.3 | A |
| Comparative Example 1 | 8.4 | A |

Example 2-1

Sertraline hydrochloride, pirotiodecane, sodium acetate, acetic acid, and liquid paraffin were put into a mortar and mixed well. This mixture was added into a mixed solution consisting of a polyisobutylene, an acrylic polymer substantially having no carboxyl and no hydroxyl (a 2-ethylhexyl acrylate.vinyl acetate copolymer), a hydrogenated rosin ester (ESTER GUM H available from ARAKAWA CHEMICAL INDUSTRIES, LTD.), ethyl acetate, and toluene to prepare a coating solution having the following composition:

polyisobutylene 20.0%
acrylic polymer 10.0%
hydrogenated rosin ester 28.0%
liquid paraffin 28.0%
pirotiodecane 3.0%
sodium acetate 3.0%
acetic acid 3.0%
sertraline hydrochloride 5.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 2.

Example 2-2

A patch agent was prepared in the same manner as in Example 2-1 except that a styrene-isoprene-styrene block copolymer was used instead of the polyisobutylene in Example 2-1.

The patch agent obtained was subjected to the skin permeability test and the preparation property test in the same manner as in Example 1. The results obtained are presented in Table 2.

Comparative Example 2

A patch agent was prepared in the same manner as in Example 2-1 except that the polyisobutylene was not used, and the patch agent was subjected to the skin permeability test and the preparation property test. The results obtained are presented in Table 2.

TABLE 2

| | Permeation rate [µg · h$^{-1}$ · m$^{-2}$] | Preparation properties |
|---|---|---|
| Example 2-1 | 15.4 | A |
| Example 2-2 | 18.8 | A |
| Comparative Example 2 | 5.0 | B |

Example 3

Pergolide mesylate, glycerol monocaprylate, sodium acetate, acetic acid, and liquid paraffin were put into a mortar and mixed well. This mixture was added into a mixed solution consisting of a styrene-isoprene-styrene block copolymer, an acrylic polymer substantially having no carboxyl and no hydroxyl (DURO-TAK87-4098 available from National Starch and Chemical Company), an aliphatic hydrocarbon resin (Quintone B170 available from ZEON CORPORATION), ethyl acetate, and toluene to prepare a coating solution having the following composition:

styrene-isoprene-styrene block copolymer 10.0%
acrylic polymer 25.0%
alicyclic saturated hydrocarbon resin 33.0%
liquid paraffin 18.0%
glycerol monocaprylate 5.0%
sodium acetate 3.0%
acetic acid 3.0%
pergolide mesylate 3.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 3.

Comparative Example 3

A patch agent was prepared in the same manner as in Example 3 except that an acrylic polymer having hydroxyls (DURO-TAK87-2287 available from National Starch and Chemical Company) was used instead of the acrylic polymer used in Example 3, and the patch agent was subjected to the skin permeability test and the preparation property test. The results obtained are presented in Table 3.

TABLE 3

|  | Permeation rate [µg · h$^{-1}$ · m$^{-2}$] | Preparation properties |
|---|---|---|
| Example 3 | 3.7 | A |
| Comparative Example 3 | 0.3 | A |

Example 4-1

Pergolide mesylate, pirotiodecane, sodium acetate, and liquid paraffin were put into a mortar and mixed well. This mixture was added into a mixed solution consisting of a styrene-isoprene-styrene block copolymer, a polyisobutylene, an acrylic polymer substantially having no carboxyl and no hydroxyl (a 2-ethylhexyl acrylate.N-vinyl-2-pyrrolidone.1,6-hexane glycol dimethacrylate copolymer), an alicyclic saturated hydrocarbon resin (ARKON P-100 available from ARAKAWA CHEMICAL INDUSTRIES, LTD.), ethyl acetate, and toluene to prepare a coating solution having the following composition:
 styrene-isoprene-styrene block copolymer 12.0%
 polyisobutylene 15.0%
 acrylic polymer 27.0%
 alicyclic saturated hydrocarbon resin 20.0%
 liquid paraffin 18.0%
 pirotiodecane 2.0%
 sodium acetate 3.0%
 pergolide mesylate 3.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 4.

Example 4-2

A patch agent was prepared in the same manner as in Example 4-1 except that the styrene-isoprene-styrene block copolymer was not used.

The patch agent obtained was subjected to the skin permeability test and the preparation property test in the same manner as in Example 1. The results obtained are presented in Table 4.

Comparative Example 4

A patch agent was prepared in the same manner as in Example 4 except that the styrene-isoprene-styrene block copolymer and polyisobutylene were not used, and the patch agent was subjected to the skin permeability test and the preparation property test. The results obtained are presented in Table 4.

TABLE 4

|  | Permeation rate [µg · h$^{-1}$ · m$^{-2}$] | Preparation properties |
|---|---|---|
| Example 4-1 | 1.7 | A |
| Example 4-2 | 2.2 | A |
| Comparative Example 4 | 0.4 | A |

Example 5

Procaterol, pirotiodecane, sodium acetate, acetic acid, and liquid paraffin were put into a mortar and mixed well. This mixture was added into a mixed solution consisting of a styrene-isoprene-styrene block copolymer, an acrylic polymer substantially having no carboxyl and no hydroxyl (a 2-ethylhexyl acrylate.vinyl acetate copolymer), a terpene resin (CLEARON P-125 available from YASUHARA CHEMICAL CO., LTD.), ethyl acetate, and toluene to prepare a coating solution having the following composition:
 styrene-isoprene-styrene block copolymer 20.0%
 acrylic polymer 18.0%
 terpene resin 21.0%
 liquid paraffin 27.0%
 pirotiodecane 3.0%
 sodium acetate 2.0%
 acetic acid 4.0%
 procaterol 5.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 5.

Comparative Example 5

A patch agent was prepared in the same manner as in Example 5 except that the styrene-isoprene-styrene block copolymer was not used, and the patch agent was subjected to the skin permeability test and the preparation property test. The results obtained are presented in Table 5.

TABLE 5

|  | Permeation rate [µg · h$^{-1}$ · m$^{-2}$] | Preparation properties |
|---|---|---|
| Example 5 | 3.0 | A |
| Comparative Example 5 | 0.8 | B |

Example 6

Procaterol hydrochloride, lauryl alcohol, sodium acetate, and liquid paraffin were put into a mortar and mixed well. This mixture was added into a mixed solution consisting of a styrene-isoprene-styrene block copolymer, an acrylic polymer substantially having no carboxyl and no hydroxyl (a 2-ethylhexyl acrylate.N-vinyl-2-pyrrolidone.1,6-hexane glycol dimethacrylate copolymer), a hydrogenated rosin ester (KE-311 available from ARAKAWA CHEMICAL INDUS- TRIES, LTD.), ethyl acetate, and toluene to prepare a coating solution having the following composition:
    styrene-isoprene-styrene block copolymer 22.0%
    acrylic polymer 18.0%
    hydrogenated rosin ester 25.0%
    liquid paraffin 24.0%
    lauryl alcohol 3.0%
    sodium acetate 3.0%
    procaterol hydrochloride 5.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 6.

Comparative Example 6

A patch agent was prepared in the same manner as in Example 6 except that the acrylic polymer was not used, and the patch agent was subjected to the skin permeability test and the preparation property test. The results obtained are presented in Table 6.

TABLE 6

|  | Permeation rate [$\mu g \cdot h^{-1} \cdot m^{-2}$] | Preparation properties |
|---|---|---|
| Example 6 | 1.9 | A |
| Comparative Example 6 | 0.9 | B |

Example 7

Oxybutynin hydrochloride, polyoxyethylene lauryl ether, sodium acetate, and liquid paraffin were put into a mortar and mixed well. This mixture was added into a mixed solution consisting of a styrene-isoprene-styrene block copolymer, an acrylic polymer substantially having no carboxyl and no hydroxyl (DURO-TAK87-4098 available from National Starch and Chemical Company), a terpene resin (CLEARON P-125 available from YASUHARA CHEMICAL CO., LTD.), ethyl acetate, and toluene to prepare a coating solution having the following composition:
    styrene-isoprene-styrene block copolymer 19.0%
    acrylic polymer 12.0%
    terpene resin 29.0%
    liquid paraffin 25.0%
    polyoxyethylene lauryl ether 3.0%
    sodium acetate 2.0%
    oxybutynin hydrochloride 10.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 7.

Comparative Example 7

A patch agent was prepared in the same manner as in Example 7 except that an acrylic polymer having carboxyls (DURO-TAK87-2852 available from National Starch and Chemical Company) was used instead of the acrylic polymer used in Example 7, and the patch agent was subjected to the skin permeability test and the preparation property test. The results obtained are presented in Table 7.

TABLE 7

|  | Permeation rate [$\mu g \cdot h^{-1} \cdot m^{-2}$] | Preparation properties |
|---|---|---|
| Example 7 | 17.6 | A |
| Comparative Example 7 | 6.8 | A |

Example 8

Oxybutynin hydrochloride, sodium acetate, and liquid paraffin were put into a mortar and mixed well. This mixture was added into a mixed solution consisting of a styrene-isoprene-styrene block copolymer, an acrylic polymer substantially having no carboxyl and no hydroxyl (a 2-ethylhexyl acrylate.vinyl acetate copolymer), an alicyclic saturated hydrocarbon resin (ARKON P-100 available from ARAKAWA CHEMICAL INDUSTRIES, LTD.), ethyl acetate, and toluene to prepare a coating solution having the following composition:
    styrene-isoprene-styrene block copolymer 20.0%
    acrylic polymer 3.0%
    alicyclic saturated hydrocarbon resin 39.0%
    liquid paraffin 25.0%
    sodium acetate 3.0%
    oxybutynin hydrochloride 10.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 8.

Comparative Example 8

A patch agent was prepared in the same manner as in Example 8 except that an acrylic polymer having hydroxyls (a 2-ethylhexyl acrylate.vinyl acetate.methacrylic acid hydroxy ester copolymer) was used instead of the acrylic polymer used in Example 8, and the patch agent was subjected to the skin permeability test and the preparation property test. The results obtained are presented in Table 8.

TABLE 8

|  | Permeation rate [$\mu g \cdot h^{-1} \cdot m^{-2}$] | Preparation properties |
|---|---|---|
| Example 8 | 20.0 | A |
| Comparative Example 8 | 7.4 | A |

Example 9

Ondansetron hydrochloride, sorbitan monolaurate, sodium acetate, and liquid paraffin were put into a mortar and mixed well. This mixture was added into a mixed solution consisting of a styrene-isoprene-styrene block copolymer, a polyisobutylene, an acrylic polymer substantially having no carboxyl and no hydroxyl (a 2-ethylhexyl acrylate.vinyl acetate copolymer), a terpene resin (CLEARON P-125 available from YASUHARA CHEMICAL CO., LTD.), ethyl acetate, and toluene to prepare a coating solution having the following composition:

styrene-isoprene-styrene block copolymer 18.0%
polyisobutylene 8%
acrylic polymer 14.0%
terpene resin 25.0%
liquid paraffin 25.0%
sorbitan monolaurate 3.0%
sodium acetate 2.0%
ondansetron hydrochloride 5.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 9.

Comparative Example 9

A patch agent was prepared in the same manner as in Example 9 except that the acrylic polymer was not used, and the patch agent was subjected to the skin permeability test and the preparation property test. The results obtained are presented in Table 9.

TABLE 9

|  | Permeation rate [$\mu g \cdot h^{-1} \cdot m^{-2}$] | Preparation properties |
|---|---|---|
| Example 9 | 38.5 | A |
| Comparative Example 9 | 21.1 | B |

Example 10

Ondansetron, lactic acid, and liquid paraffin were put into a mortar and mixed well. This mixture was added into a mixed solution consisting of a styrene-isoprene-styrene block copolymer, an acrylic polymer substantially having no carboxyl and no hydroxyl (a 2-ethylhexyl acrylate.N-vinyl-2-pyrrolidone.1,6-hexane glycol dimethacrylate copolymer), an alicyclic saturated hydrocarbon resin (ARKON P-100 available from ARAKAWA CHEMICAL INDUSTRIES, LTD.), ethyl acetate, and toluene to prepare a coating solution having the following composition:

styrene-isoprene-styrene block copolymer 22.0%
acrylic polymer 20.0%
alicyclic saturated hydrocarbon resin 31.0%
liquid paraffin 19.0%
lactic acid 3.0%
ondansetron 5.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 10.

Comparative Example 10

A patch agent was prepared in the same manner as in Example 10 except that the acrylic polymer was not used, and the patch agent was subjected to the skin permeability test and the preparation property test. The results obtained are presented in Table 10.

TABLE 10

|  | Permeation rate [$\mu g \cdot h^{-1} \cdot m^{-2}$] | Preparation properties |
|---|---|---|
| Example 10 | 25.1 | A |
| Comparative Example 10 | 19.8 | B |

Example 11-1

Oxybutynin hydrochloride, citric acid, sodium acetate, and liquid paraffin were put into a mortar and mixed well. This mixture was added into a mixed solution consisting of a styrene-isoprene-styrene block copolymer, an acrylic polymer substantially having no carboxyl and no hydroxyl (an aminoalkylmethacrylate copolymer E), an aliphatic saturated hydrocarbon resin (ARKON P-100 available from ARAKAWA CHEMICAL INDUSTRIES, LTD.), ethyl acetate, and toluene to prepare a coating solution having the following composition:

styrene-isoprene-styrene block copolymer 19.5%
acrylic polymer 4.0%
alicyclic saturated hydrocarbon resin 24.0%
liquid paraffin 35.0%
citric acid 1.5%
sodium acetate 6.0%
oxybutynin hydrochloride 10.0%.

Then the resultant coating solution was applied onto polyethylene terephthalate release paper, and dried to remove the solvent to form the adhesive layer, and the polyethylene terephthalate support was attached to the adhesive layer to obtain the objective patch agent.

The patch agent obtained was subjected to the skin permeability test and the preparation property test in the same manner as in Example 1. The results obtained are presented in Table 11.

Example 11-2

A patch agent was prepared in the same manner as in Example 11-1 except that the coating solution used was one having the composition below:

styrene-isoprene-styrene block copolymer 15.5%
polyisobutylene 4.0%
acrylic polymer 4.0%
alicyclic saturated hydrocarbon resin 24.0%
liquid paraffin 35.0%
citric acid 1.5%
sodium acetate 6.0%
oxybutynin hydrochloride 10.0%

The patch agent obtained was subjected to the skin permeability test and the preparation property test in the same manner as in Example 1. The results obtained are presented in Table 11.

Example 11-3

A patch agent was prepared in the same manner as in Example 11-1 except that the acrylic polymer used was a 2-ethylhexyl acrylate.N-vinyl-2-pyrrolidone.1,6-hexane glycol dimethacrylate copolymer instead of the aminoalkylmethacrylate copolymer E.

The patch agent obtained was subjected to the skin permeability test and the preparation property test in the same manner as in Example 1. The results obtained are presented in Table 11.

Example 11-4

A patch agent was prepared in the same manner as in Example 11-1 except that the acrylic polymer used was a 2-ethylhexyl acrylate.vinyl acetate copolymer instead of the aminoalkylmethacrylate copolymer E.

The patch agent obtained was subjected to the skin permeability test and the preparation property test in the same manner as in Example 1. The results obtained are presented in Table 11.

Comparative Example 11

A patch agent was prepared in the same manner as in Example 11-1 except that the styrene-isoprene-styrene block copolymer was not used.

The patch agent obtained was subjected to the skin permeability test and the preparation property test in the same manner as in Example 1. The results obtained are presented in Table 11.

TABLE 11

|  | Permeation rate $[\mu g \cdot h^{-1} \cdot m^{-2}]$ | Preparation properties |
|---|---|---|
| Example 11-1 | 11.3 | A |
| Example 11-2 | 17.7 | A |
| Example 11-3 | 22.5 | A |
| Example 11-4 | 24.2 | A |
| Comparative Example 10 | 4.9 | B |

As apparent from Tables 1-11, it was confirmed that all the patch agents of Examples 1 to 11-4 demonstrated the sufficiently high skin permeation and preparation properties.

INDUSTRIAL APPLICABILITY

As described above, the patch agents of the present invention demonstrated the sufficiently high skin permeation of the drug and preparation properties and presented the drug administration effect at a sufficiently high level and on a stable basis in administration of the drug through skin.

The invention claimed is:
1. A patch, comprising:
a support; and
an adhesive layer consisting of
a styrene-isoprene-styrene block copolymer,
a 2-ethylhexyl acrylate-N-vinyl-2-pyrrolidone.1-,6-hexane glycol dimethacrylate copolymer,
an alicyclic saturated hydrocarbon resin,
a liquid paraffin,
glycerol monocaprylate,
sodium acetate,
acetic acid, and
pergolide mesylate.
2. A patch, comprising:
a support; and
an adhesive layer consisting of
a styrene-isoprene-styrene block copolymer,
polyisobutylene,
a 2-ethylhexyl acrylate.N-vinyl-2-pyrrolidone.1,6-hexane glycol dimethacrylate copolymer,
an alicyclic saturated hydrocarbon resin,
a liquid paraffin,
pirotiodecane,
sodium acetate, and
pergolide mesylate.
3. A patch, comprising:
a support; and
an adhesive layer consisting of
a styrene-isoprene-styrene block copolymer,
a 2-ethylhexyl acrylate-N-vinyl-2-pyrrolidone.1-,6-hexane glycol dimethacrylate copolymer,
a terpene resin,
a liquid paraffin,
polyoxyethylene lauryl ether,
sodium acetate, and
oxybutynin hydrochloride.
4. A patch, comprising:
a support; and
an adhesive layer consisting of
a styrene-isoprene-styrene block copolymer,
an aminoalkylmethacrylate copolymer E,
an alicyclic saturated hydrocarbon resin,
a liquid paraffin,
citric acid,
sodium acetate, and
oxybutynin hydrochloride.
5. A patch, comprising:
a support; and
an adhesive layer laid on the support, the adhesive layer consisting of
a styrene-isoprene-styrene block copolymer,
polyisobutylene,
an aminoalkylmethacrylate copolymer E,
an alicyclic saturated hydrocarbon resin,
a liquid paraffin,
citric acid,
sodium acetate, and
oxybutynin hydrochloride.

* * * * *